(12) United States Patent
Blickhan

(10) Patent No.: US 7,332,096 B2
(45) Date of Patent: Feb. 19, 2008

(54) BLOOD FILTER ASSEMBLY HAVING MULTIPLE FILTRATION REGIONS

(75) Inventor: Bryan J Blickhan, Zion, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 10/742,521

(22) Filed: Dec. 19, 2003

(65) Prior Publication Data

US 2005/0133439 A1  Jun. 23, 2005

(51) Int. Cl.
*B01D 37/00* (2006.01)

(52) U.S. Cl. .................. 210/767; 210/335; 210/435; 210/456; 210/459; 210/489; 604/406

(58) Field of Classification Search .............. 210/323.1, 210/321.75, 321.84, 435, 446, 456, 459, 210/499, 645, 650, 767, 232, 335, 503, 505, 210/489; D24/162; 422/101, 102; 604/406, 604/408, 410
See application file for complete search history.

(56) References Cited

U.S. PATENT DOCUMENTS

| | | | |
|---|---|---|---|
| 3,567,028 A * | 3/1971 | Nose | 210/232 |
| 4,304,670 A | 12/1981 | Watanabe et al. | |
| 4,340,670 A * | 7/1982 | Mennen | 435/25 |
| D367,326 S * | 2/1996 | Bormann et al. | D24/162 |
| 5,772,880 A * | 6/1998 | Lynn et al. | 210/435 |
| 6,231,770 B1 * | 5/2001 | Bormann et al. | 210/767 |
| 6,660,171 B2 * | 12/2003 | Zuk, Jr. | 210/767 |
| 6,688,476 B2 * | 2/2004 | Breillatt, Jr. et al. | 210/435 |
| 2002/0063090 A1 * | 5/2002 | Calhoun et al. | 210/321.6 |

FOREIGN PATENT DOCUMENTS

FR    2 821 762    3/2001

\* cited by examiner

*Primary Examiner*—Joseph Drodge
(74) *Attorney, Agent, or Firm*—Cook, Alex, McFarron, Manzo, Cummings & Mehler, Ltd.

(57) ABSTRACT

A filtration medium is sealed within a housing. The filtration medium is sized and configured to define multiple filtration regions within the housing, through which independent, though concurrent, blood filtration can occur. Each filtration region is served by its own inlet path, which conveys blood into the filtration region. The filtration medium in each filtration region passes the blood to remove at least one undesired component, such as, e.g., leukocytes. After filtration, the multiple filter regions convey the blood into a single, centrally located manifold. A single outlet path communicates with the manifold.

12 Claims, 6 Drawing Sheets

BLOOD FILTER ASSEMBLY HAVING MULTIPLE FILTRATION REGIONS

FIELD OF THE INVENTION

The invention generally relates to filters used in the collection and processing of blood and blood components.

BACKGROUND OF THE INVENTION

Using various manual and automated systems, whole blood is collected and separated into its clinical components (typically red blood cells, platelets, and plasma). The components are individually stored and used to treat a multiplicity of specific conditions and diseased states.

Before storing blood components for later transfusion, or before subjecting blood components to treatment such as pathogen inactivation, it is believed to be desirable to minimize the presence of impurities or other materials that may cause undesired side effects in the recipient. For example, because of possible reactions, it is generally considered desirable to reduce the number of leukocytes in blood components before storage, or at least before transfusion.

Filters are widely used to accomplish leuko-reduction in blood products today. Consequently, there is an on-going impetus to improve the construction, performance, and manufacturability of blood filters today.

SUMMARY OF THE INVENTION

A blood filter assembly is provided that comprises a filtration medium sealed within a housing. The filtration medium is sized and configured to define multiple filtration regions within the housing, through which independent, though concurrent, blood filtration can occur. Each filtration region is served by its own inlet path, which conveys blood into the filtration region. The filtration medium in each filtration region passes the blood to remove at least one undesired component, such as, e.g., leukocytes. After filtration, the multiple filter regions convey the blood into a single manifold, which is centrally located within the filter assembly. A single outlet path communicates with the manifold, to convey filtered blood from the filter assembly.

In one embodiment, the housing is flexible. In a desired arrangement, the filter medium and flexible housing are peripherally sealed by the application of pressure and radio frequency energy in a single processing step.

The filter assembly makes possible the establishment of independent, but concurrent, flow paths through multiple filtration regions. Multiple filtration regions multiply the effective surface area of medium available for filtration, mitigating against stoppage or reduction of blood flow through the filter assembly, as well as making more effective use of a given volume of filtration medium over time.

A centralized outlet path drives negative pressure generated at the completion of filtration to the inside of the filter assembly. Although the filter housing may be flexible, there is no collapse of the housing due to the presence of negative pressure. There is no "air lock" to prevent the outlet side from draining.

The filter assembly can be integrated in different ways into multiple blood bag systems or automated blood processing systems to remove undesired components like leukocytes from whole blood, red blood cells, platelet-rich plasma, platelet-poor plasma, and/or platelet concentrate prior to storage and/or transfusion and/or pathogen inactivation.

Other features and advantages of the invention will become apparent upon review of the following description, drawings, and appended claims.

Figure 1:
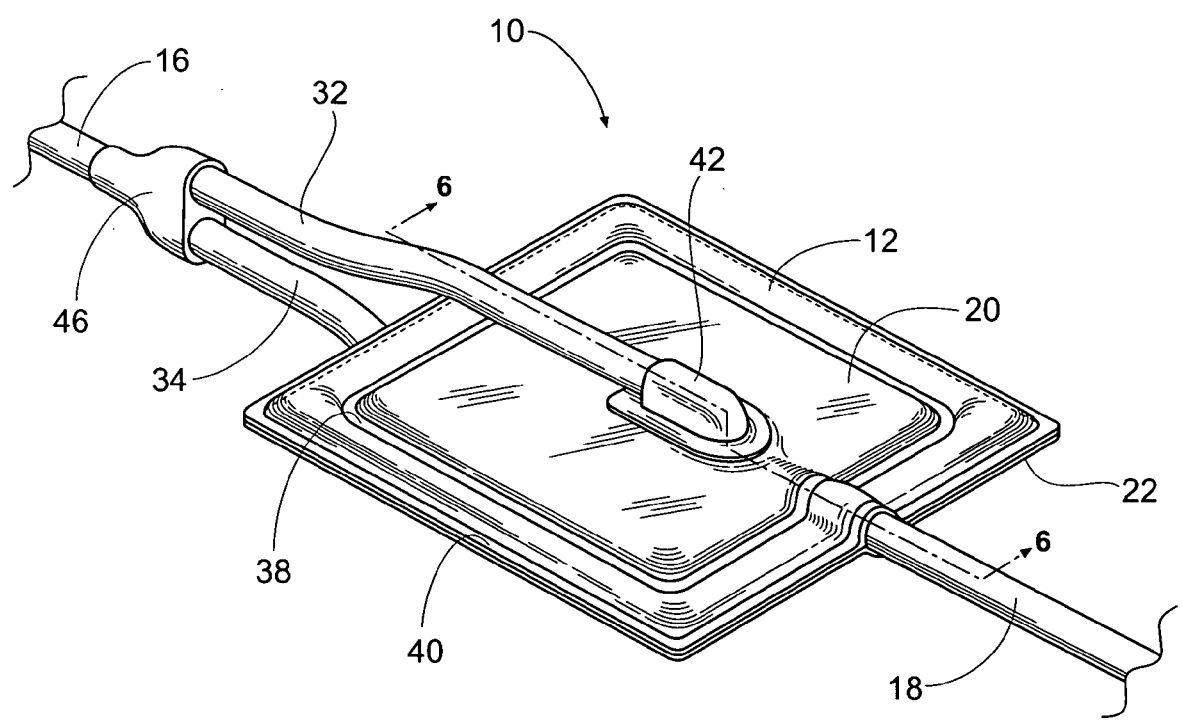
FIG. 1 is a perspective view of a blood filter assembly.

The invention is not limited to the details of the construction and the arrangements of parts set forth in the following description or shown in the drawings. The invention can be practiced in other embodiments and in various other ways. The terminology and phrases are used for description and should not be regarded as limiting.

DESCRIPTION OF THE PREFERRED EMBODIMENTS

Figure 2:
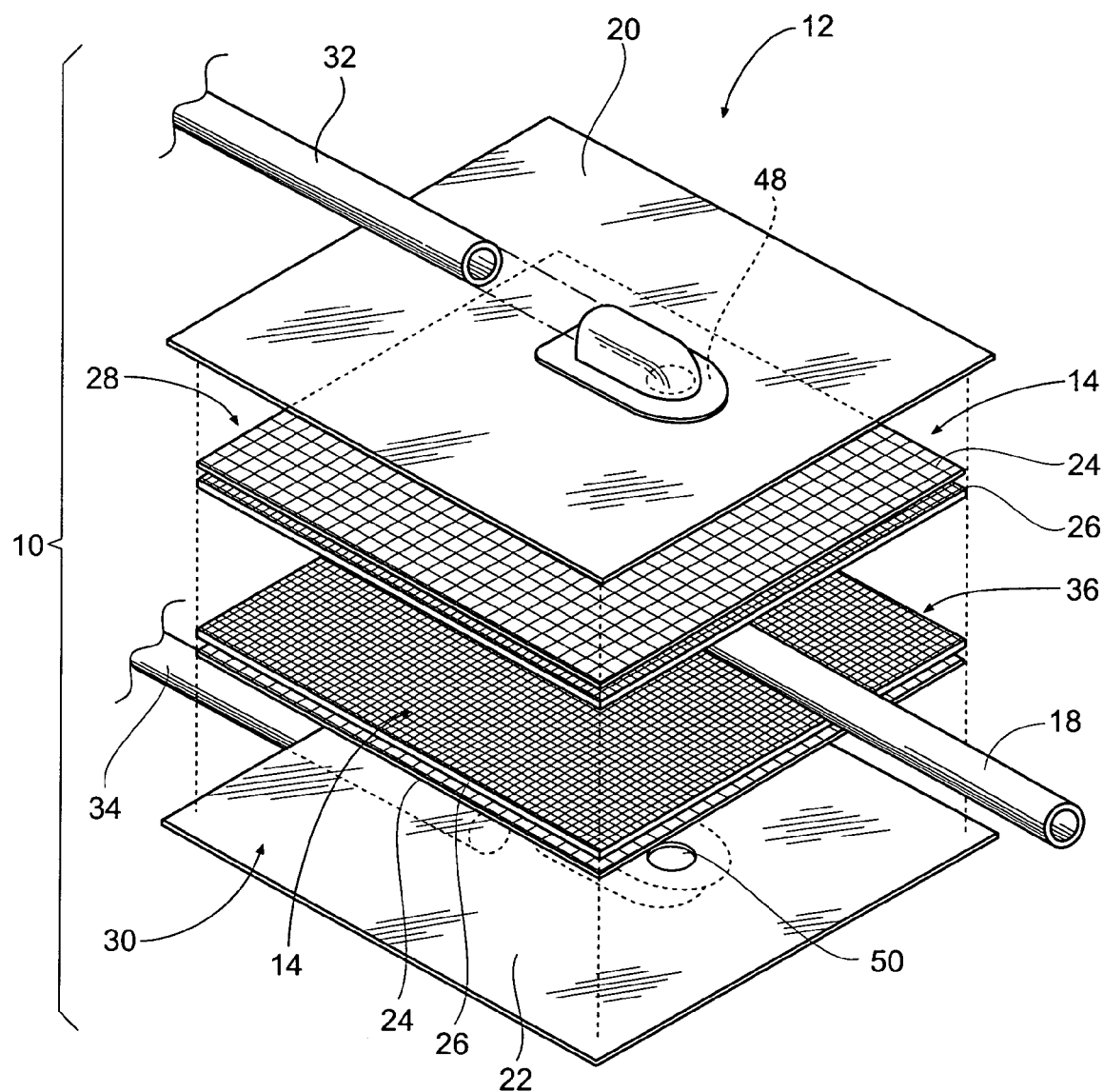
FIG. 2 is an exploded perspective view of the blood filter assembly shown in FIG. 1.

FIGS. 1 and 2 show a blood filter assembly 10. The blood filter assembly 10 is configured to be used in the collection and/or processing of blood and blood components by either manual or automated fashion. In the illustrated embodiments, the blood filter is intended, during use, to selectively remove leukocytes from whole blood or components of whole blood, such as red blood cells, platelets, or plasma.

The filter assembly 10 includes a housing 12. The housing 12 encloses a blood filtration medium 14, as FIG. 2 shows. An inlet 16 conveys blood into the housing for passage through the blood filtration medium 14. An outlet 18 conveys blood from the housing after passage through the blood filtration medium 14.

The filter assembly 10 is intended to be a disposable, single use item. The filter housing 12 is desirably made using conventional approved medical grade plastic materials. Such material cans be rigid or semi-rigid, in which case the housing 12 can be molded or machined to the desired size and configuration.

Desirably, as shown in the embodiment illustrated in FIGS. 1 and 2, the filter housing 12 is made from a flexible plastic material. The filter assembly 10, being flexible, facilitates handling and reduces the incidence of damage to other plastic components used in association with the filter assembly 10 for a given blood processing procedure. The use of flexible plastic material also enables the use of conventional radio frequency heat sealing technology to seal the filter assembly 10, as will be described in greater detail later.

In the particular embodiment shown in FIG. 2, the housing comprises first and second sheets 20 and 22 of medical grade plastic material, such as polyvinyl chloride plasticized with di-2-ethylhexyl-phthalate (PVC-DEHP). Other medical grade plastic materials can be used that are not PVC and/or are DEHP-free, provided that the material heats and flows when exposed to radio frequency energy.

The filtration medium 14 can be variously constructed, e.g., from porous membrane materials or fibers, depending upon the objectives of filtration and the nature of the blood component being filtered. In the illustrated embodiment, the filtration medium 14 is made from a fibrous material, which is sandwiched between the sheets 20 and 22. The medium 14 can include melt blown or spun bonded synthetic fibers (e.g., nylon or polyester or polypropylene), semi-synthetic fibers, regenerated fibers, or inorganic fibers. In use, the medium 14 removes leukocytes by principally by depth filtration, as compared to removal by size exclusion.

The filtration medium 14 is desirably sized and configured to form more than a single filtration region. In the embodiment shown in FIG. 2, two filtration regions 28 and 30 are shown (see FIG. 6) for the purpose of illustration, although more than two filtration regions can exist.

Figure 6:
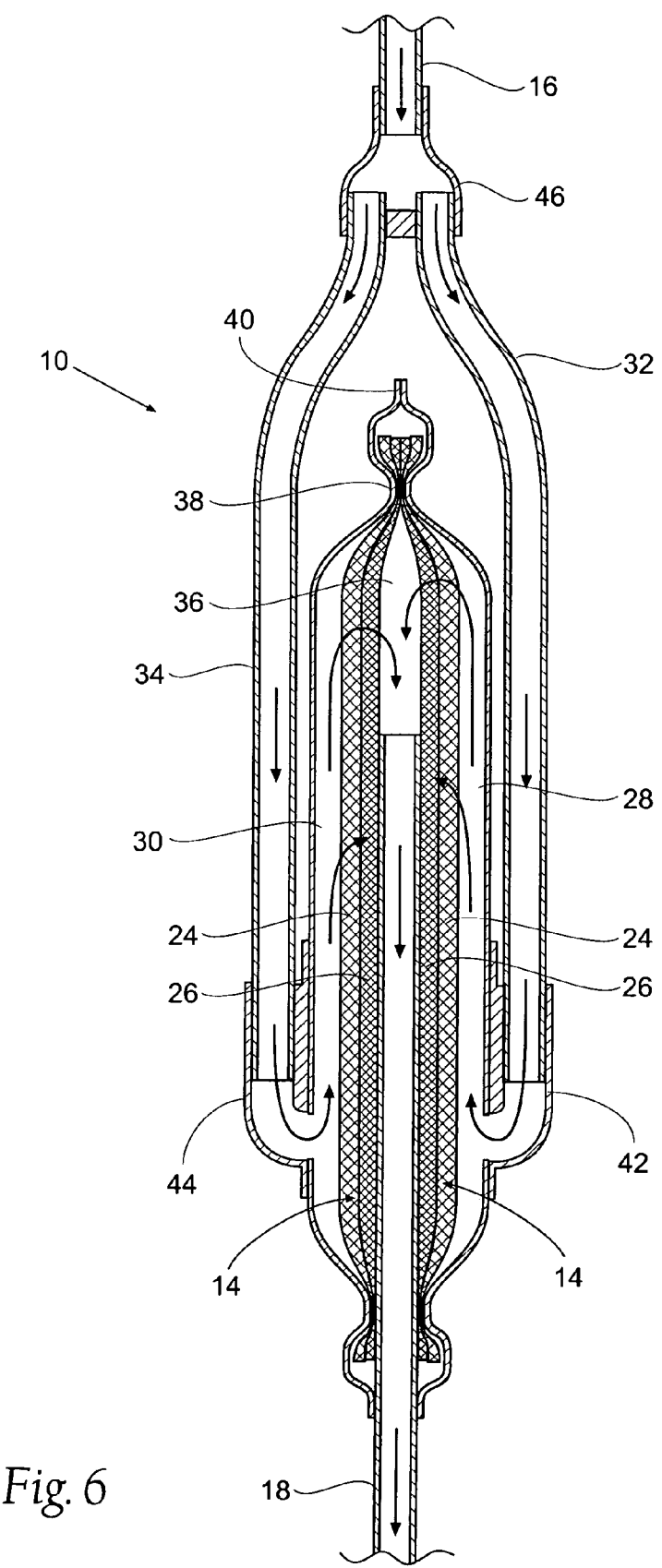
FIG. 6 is a side sectional view of the blood filter assembly taken generally along line 6-6 in FIG. 1, showing multiple filtration regions and the path that blood follows through the multiple filtration regions.

As FIG. 6 best shows, blood entering the filter assembly 10 through the inlet 16 is directed to the different filtration regions by separate flow paths. In the illustrated embodiment, where there are two filtration regions 28 and 30, there are two flow paths 32 and 34. One flow path 32 directs the blood into the first filtration region 28. The other flow path 34 directs the blood into the second filtration region 30. The number of flow paths can vary, provided that there is at least one flow path serving each filtration region.

In the illustrated embodiment, the inlet 16 comprises flexible tubing made, e.g., of PVC-DEHP material. Each flow path 32 and 34 likewise comprises a length of flexible tubing made of the same or different material. A junction 44 joins the tubing flow paths 32 and 34 to the inlet tubing 16.

The filter assembly 10 channels the blood through each filtration region 28 and 30 and into a common, centrally located post-filtration manifold 36 (see FIG. 6). The outlet 18 communicates with this manifold 36, to convey blood, after filtration, from the filter assembly 10. In the illustrated embodiment, the outlet 18 comprises flexible tubing made, e.g., of PVC-DEHP material. Also, in the illustrated embodiment, the outlet 18 extends along the centerline of manifold 36.

Alternatively, the outlet 18 can comprise a rigid tube. The outlet 18 can be straight (as shown) or curvilinear. The outlet 18 can comprise a single flow path (as shown) or comprise multiple branches. The outlet 18 is desirably formed in a manner that directs adequate and uniform flow of blood from the filter assembly.

The filtration medium 14 in each filtration region 28 and 30 can be the same, or it can differ, depending upon the objectives of filtration and the nature of the blood component being filtered. Also, the filtration medium 14 in each filtration region 28 and 30 can be arranged in a single layer or in a multiple layer stack. In the illustrated embodiment, the filtration medium 14 in each filtration region 28 and 30 is the same, and it includes two layers 24 and 26.

The layer 24 comprises a prefilter. The prefilter layer 24 is oriented in the blood flow direction in each filtration region to contact blood first. The prefilter layer 24 is sized to remove gross clots and aggregations present in the blood. In a representative embodiment, e.g., in which the filter assembly 10 is used to filter blood that contains red blood cells or platelets, the prefilter layer 24 is made of fibrous material (e.g., polyethylene) having a pore size of between about 15 µm to about 20 µm.

The layer 26 comprises a main filter. The main filter layer 26 is oriented in the blood flow direction in each filtration region to contact blood after passage through the prefilter layer 24. The main filter layer 26 has a pore size and fiber diameter sized to remove leukocytes by depth filtration. In a representative embodiment, e.g., in which the filter assembly 10 is used to filter blood that contains red blood cells or platelets, the main filter layer 26 is made of a fibrous material (e.g., polyethylene) having the characteristics described in Watanabe et al. U.S. Pat. No. 4,701,267 or Nishimura et al. U.S. Pat. No. 4,936,998, which are incorporated herein by reference.

In the illustrated embodiment, for each filtration region 28 and 30, the two filter layers 24 and 26 of each filtration medium 14 overlay each other. The filter mediums 14 in the two filtration regions 28 and 30, in turn, overlay themselves, with the main filter layers 26 of the regions 28 and 30 mutually facing inward to define between them the manifold 36. In this arrangement, the prefilter layers 24 of the regions 28 and 30 mutually face outward toward a respective one of the housing sheets 20 and 22, which sandwich the filtration medium 14 together.

In a desired embodiment, a unitary, continuous main seal 38 is formed by the application of pressure and radio frequency heating in a single process steps to the two sheets 20 and 22 and the filtration medium 14. The main seal 38 joins the two sheets 20 and 22 to each other, as well as joins the filtration medium 14 to the two sheets 20 and 22. The main seal 38 integrates the material of the filtration medium 14 and the material of the plastic sheets 20 and 22, providing a reliable, robust, leak-proof boundary. Since the main seal 38 is unitary and continuous, the possibility of blood shunting around the periphery of the filtration medium 14 is eliminated. If desired, a peripheral seal 40, outboard of the main seal 38, can be formed by radio frequency heating to join the peripheries of the sheets 20 and 22.

In this arrangement, the filter assembly 10 includes two inlet ports 42 and 44. The port 42 is coupled to the tubing flow path 32, to direct the blood into the first filtration region 28. The port 44 is coupled to the tubing flow path 34, to direct the blood into the second filtration region 30.

In the illustrated embodiment, the ports 42 and 44 are located near the bottom of the inlet side of each filtration region 28 and 30 (see FIG. 6). This orientation allows effective air removal (i.e., venting) and priming. Each filtration region 28 and 30 fills with blood from the bottom up, without inversion.

In the illustrated embodiment, the ports 42 and 44 are located in a symmetric, opposed relationship. Alternatively, the ports 42 and 44 could be located in an offset relationship.

In the illustrated embodiment, the inlet ports 42 and 44 comprise separately molded parts. The ports 42 and 44 can be secured over or under holes 48 and 50 formed in the sheets 20 and 22 before the formation of the main seal 38. Alternatively, the ports 42 and 44 can be secured to the sheets 20 and 22, e.g., by heat sealing or adhesive, after the formation of the main seal 38.

In the illustrated embodiment, a portion of the outlet tubing 18 extends through the main seal 38 and into the manifold 36. The outlet tubing 18 is sealed in place in the main seal 38 at the same time that the unitary peripheral seal 38 is formed.

Figure 3:
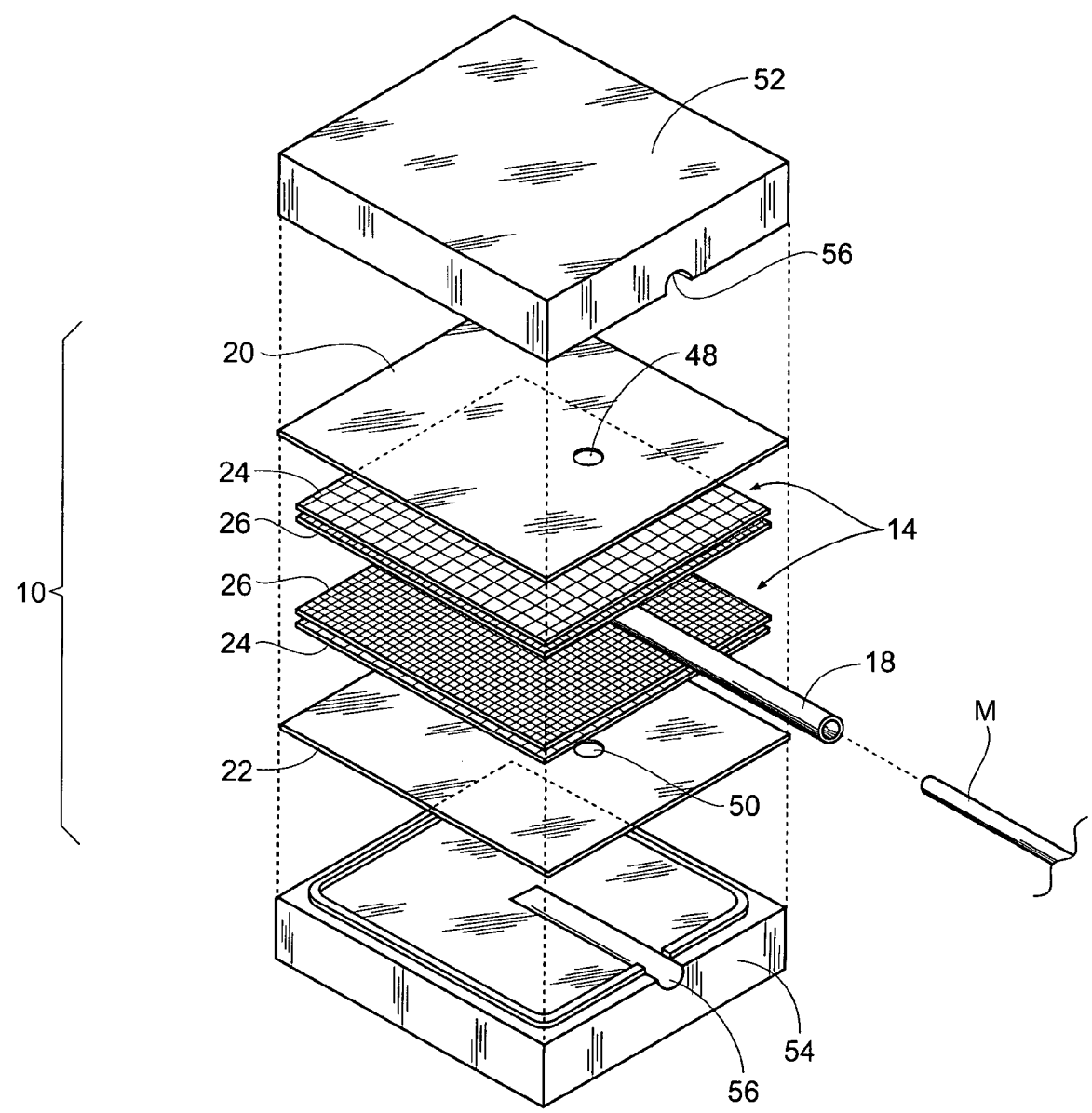
FIG. 3 is an exploded perspective view of the blood filter assembly shown in FIG. 1, in association with the dies that form the main seal of the filter assembly.

More particularly, as FIG. 3 shows, the first and second plastic sheets 20 and 22, the filtration medium 14, and the outlet tubing 18 are placed between a pair of opposed dies 52 and 54. As FIG. 3 shows, the dies 52 and 54 are provided with aligned concave recesses 56. The recesses 56 register to receive the outlet tubing 18 when the dies are brought together. When moved together, the opposed dies 52 and 54 sandwich the filter assembly 10 and apply pressure to press the peripheral edge of the filter assembly 10 together. Mandrel M is inserted into the outlet tubing 18 to prevent deformation of the tubing 18 while a hermetic seal is formed between the housing material and filtration medium around the exterior of the tubing 18.

As the dies 52 and 54 apply pressure about the peripheral edge of the filter assembly 40, radio frequency energy is applied through the dies 52 and 54. The combination of radio frequency energy and pressure softens the plastic material of the sheets 20 and 22. The applied pressure causes the heat softened material of the sheets 20 and 22 to penetrate the interstices of the filtration medium 14, creating an interior matrix of sheet material commingled with filtration medium material. Within the matrix, the filtration medium 14 melts, as the main seal 38 forms. At its surface, along the sheets 20 and 22, the seal 38 comprises mostly the material of the sheets 20 and 22. With increasing distance from the surface, the seal 38 comprises a commingled melted matrix of the material of the sheets 20 and 22 and the material of the filtration medium 14. After a brief period of cooling, the seal 38 sets and the dies 52 and 54 are withdrawn, as is the mandrel for the outlet tubing 18.

Figure 4:
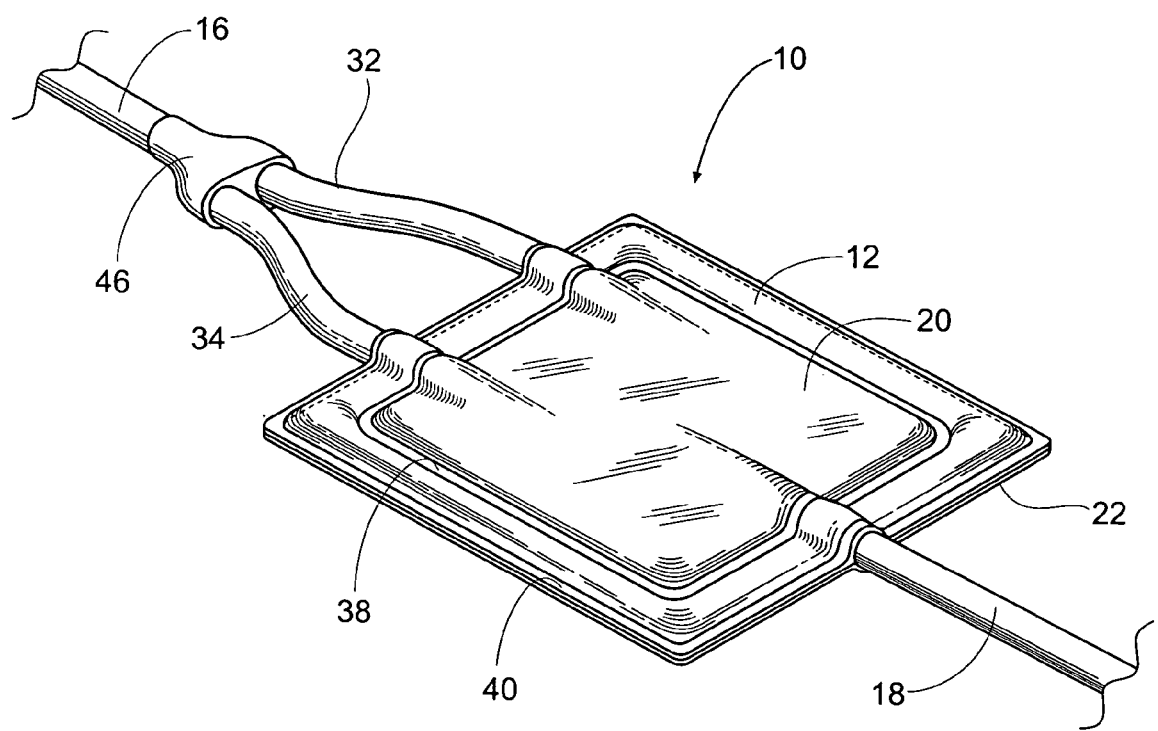
FIG. 4 is a perspective view of an alternative embodiment of a blood filter assembly.
Figure 5:
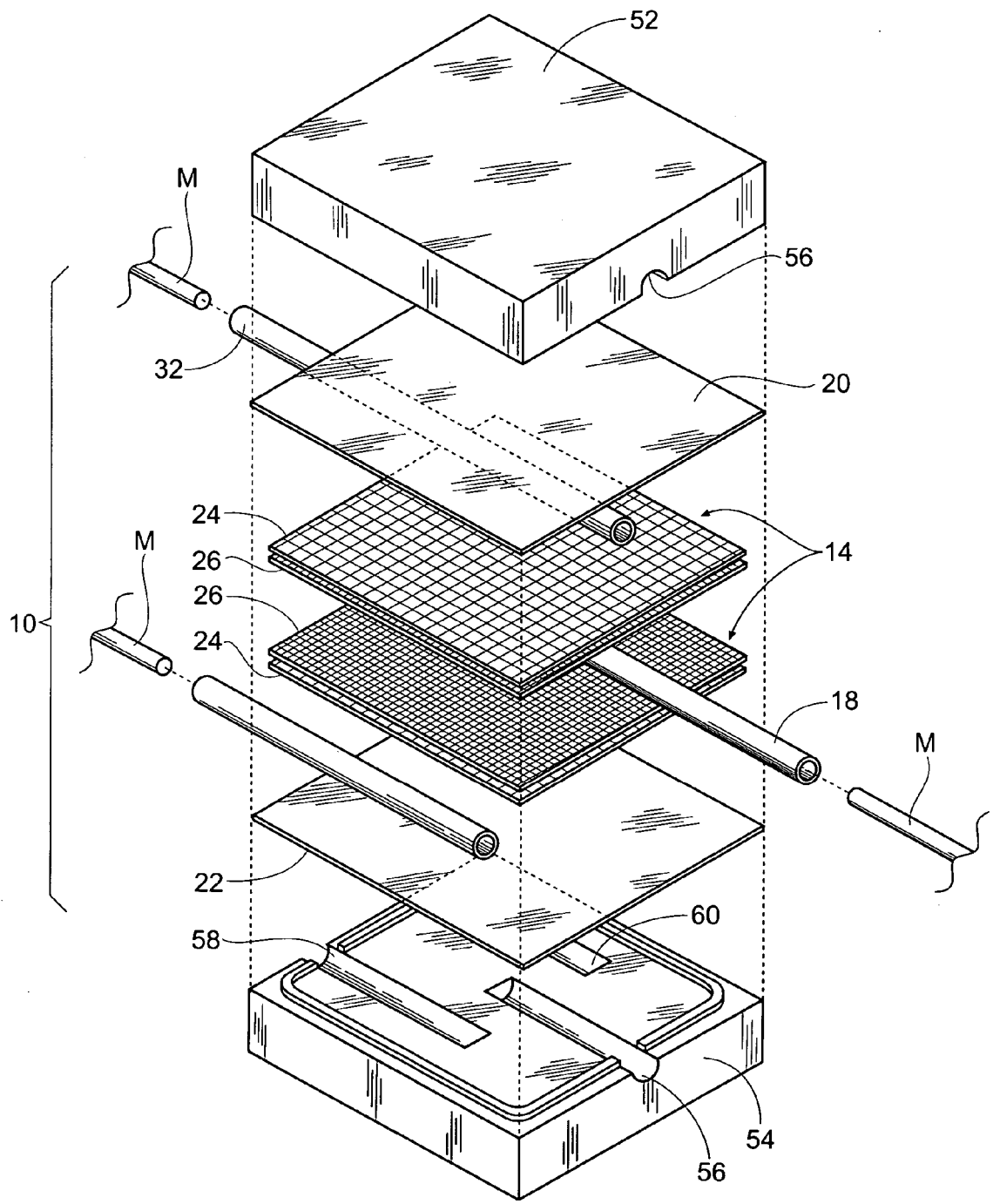
FIG. 5 is an exploded perspective view of the blood filter assembly shown in FIG. 4, in association with the dies that form the main seal of the filter assembly.

In an alternative arrangement (see FIGS. 4 and 5), the inlet tubing 32 and 34 could also extend through the main seal 38 and into the respective filtration region 28 and 30. In this arrangement, the inlet tubing 32 and 34 is sealed in place in the main seal 38 at the same time that the unitary peripheral seal 36 is formed. To accommodate this (see FIG. 5), the dies 52 and 54 are provided with additional aligned concave recesses 58 and 60. The additional recesses 58 and 60 register to receive the inlet tubing 32 and 34 when the dies are brought together. Mandrels M are inserted into the inlet tubing 32 and 34 to prevent deformation of the tubing 32 and 34 while a hermetic seal is formed between the housing material and filtration medium around the exterior of the tubing 32 and 34.

In use (see FIG. 6), blood enters through the inlet tubings 32 and 34 into contact with the two filtration regions 28 and 30. The blood can be conveyed by gravity flow, by placing the source container above the filter. Alternatively, a pump can be used to convey blood into the filter assembly at higher pressure and greater flow rates. In the illustrated embodiment, the introduction of blood into each filtration region 28 and 30 occurs concurrently, which is preferred. Being flexible, the housing 12 concurrently expands on both sides to accommodate the blood volume. In this arrangement, positive pressure can be applied simultaneously to both filtration regions 28 and 30 on opposite sides of the filter assembly 10 to drive blood flow through the medium 14.

Still, if desired, a staged introduction of blood into the first filtration region 28, and then the second filtration region 30 can be accomplished using the filter assembly 10.

In each filtration region 28 and 30, the blood flows through the filtration medium 14 inward toward the manifold 36. In the process, leukocytes are removed from the blood by depth filtration. The leukocyte-reduced blood enters the manifold 36. The outlet 18 conveys the leukocyte-reduced blood from the manifold 36 and out of the filter. In the illustrated and preferred arrangement, the flow of blood through the filtration medium 14 from each filtration region 28 and 30 occurs concurrently, at least for a portion of the filtration process.

The filter assembly 10 makes possible the establishment of multiple, independent, but concurrent, flow paths through multiple filtration regions. Multiple filtration regions multiply the effective surface area of the prefilter layer, mitigating against stoppage or reduction of blood flow through the filter. Multiple filtration regions also make available, in a given volume, more surface area for the main filter layer, thereby making more effective use of the main filter layer per unit of time.

Multiple filtration regions also simplify priming of the filtration medium 14. Furthermore, being sealed within a flexible housing 12, fluid head pressure will causes the housing to distend or expand after priming and during use, which evenly distributes the blood across the inlet face of both filtration regions 28 and 30. Also, since both regions 28 and 30 are inlets, they will both drain and clear with air at the end of filtration, resulting a greater recovery of blood from the filter assembly 10.

The centralized outlet path 18 drives negative pressure generated at the completion of filtration to the inside of the filter assembly 10. Although the filter housing 12 is flexible, there is no collapse of the housing due to the presence of negative pressure. There is no "air lock" to prevent the outlet side from draining, because both sides of the filter assembly 10 drain, since both sides are an inlet.

The filter assembly 10 can be integrated in different ways into multiple blood bag systems or automated blood processing systems to remove leukocytes from whole blood, red blood cells, platelet-rich plasma, platelet-poor plasma, and/or platelet concentrate prior to storage and/or pathogen inactivation. The flexible housing 12 will not puncture associated bags, which are also made of flexible plastic materials. Unlike a rigid housing, the flexible housing 12 conforms and is compliant to stress and pressures induced during use.

Various features of the invention are set forth in the following claims.

I claim:

1. A blood filter assembly comprising housing, a filtration medium contained within a housing comprising a flexible material, the filtration medium being sized and configured to define multiple filtration regions within the housing, the filtration regions including a top filtration portion and a bottom filtration portion, a top port communicating only with the top filtration portion, a bottom port communicating only with the bottom filtration portion, separate first and second inlet paths, the first inlet path including a first length of tubing which is coupled only to the top port and not the bottom port and which extends outside the housing for communication with a blood source to convey blood into the housing for contact only with the top filtration portion, the second inlet path including a second length of tubing which is separate from the first length of tubing and which is coupled only to the bottom port and not the top port and which extends outside the housing for communication with the blood source to convey blood into the housing for contact only with the bottom filtration portion, the separate first and second lengths of tubing dividing blood flow from the blood source into separate flow paths before entering the housing, an outlet manifold within the housing to receive blood from all filtration regions after passage through the filtration medium, and at least one outlet path communicating with the outlet manifold to convey blood from the housing;

wherein a peripheral seal joins the housing to the filtration medium and said outlet path passes through said peripheral seal.

2. An assembly according to claim 1, wherein the filtration medium in at least one of the filtration regions comprises a fibrous material.

3. An assembly according to claim 1, wherein the filtration medium in at least one of the filtration regions comprises a multiple layer structure.

4. An assembly according to claim 1, wherein the filtration in at least one of the filtration regions comprises a material that removes leukocytes from blood.

5. An assembly according to claim 1, wherein only one outlet path communicates with the outlet manifold to convey blood from the housing.

6. An assembly according to claim 5, wherein the only one outlet path extends along a centerline of the outlet manifold.

7. An assembly according to claim 5, wherein the only one outlet path extends into the outlet manifold.

8. An assembly according to claim 1, wherein at least one of the top and bottom ports is spaced from the peripheral seal.

9. An assembly according to claim 1, wherein at least one of the top and bottom ports passes through the peripheral seal.

10. An assembly according to claim 1, wherein the outlet manifold comprises a chamber formed between top and bottom filtration portions.

11. A blood collection system comprising a container, tubing coupled to the container, and a blood filter assembly as defined in claim 1 carried in-line in the tubing.

12. A method of filtering blood using the blood filter assembly as defined in claim 1.

* * * * *